(12) United States Patent
Marsh

(10) Patent No.: US 10,213,135 B2
(45) Date of Patent: Feb. 26, 2019

(54) EQUESTRIAN MONITORING AND FEEDBACK DEVICE

(71) Applicant: Robert Elliott Marsh, Kansas City, MO (US)

(72) Inventor: Robert Elliott Marsh, Kansas City, MO (US)

(*) Notice: Subject to any disclaimer, the term of this patent is extended or adjusted under 35 U.S.C. 154(b) by 554 days.

(21) Appl. No.: 14/919,454

(22) Filed: Oct. 21, 2015

(65) Prior Publication Data

US 2016/0114233 A1 Apr. 28, 2016

Related U.S. Application Data

(60) Provisional application No. 62/067,789, filed on Oct. 23, 2014.

(51) Int. Cl.

| | |
|---|---|
| *A61B 5/11* | (2006.01) |
| *G09B 19/00* | (2006.01) |
| *G01L 5/22* | (2006.01) |
| *G01L 5/16* | (2006.01) |
| *A61B 5/00* | (2006.01) |
| *A61B 5/103* | (2006.01) |
| *B68C 1/00* | (2006.01) |
| *B68C 1/16* | (2006.01) |
| *H04M 1/725* | (2006.01) |
| *G06F 19/00* | (2018.01) |

(52) U.S. Cl.
CPC .......... *A61B 5/1116* (2013.01); *A61B 5/1036* (2013.01); *A61B 5/742* (2013.01); *A61B 5/7405* (2013.01); *B68C 1/00* (2013.01); *B68C 1/16* (2013.01); *G01L 5/161* (2013.01); *G01L 5/225* (2013.01); *G09B 19/0038* (2013.01); *A61B 2503/40* (2013.01); *G06F 19/3481* (2013.01); *H04M 1/7253* (2013.01)

(58) Field of Classification Search
CPC ... A61B 5/1116; A61B 5/1036; A61B 5/7405; A61B 5/742; A61B 2503/40; B68C 1/00; B68C 1/16; G01L 5/161; G01L 5/225; G09B 19/0038; G06F 19/3481; H04M 1/7253
USPC ......................................................... 434/247
See application file for complete search history.

(56) References Cited

U.S. PATENT DOCUMENTS

| | | | | |
|---|---|---|---|---|
| 3,130,530 A | * | 4/1964 | Foreman | B68C 1/02 54/46.2 |
| 5,369,601 A | * | 11/1994 | Tannenbaum | A63B 69/00 702/139 |
| 2014/0253337 A1 | * | 9/2014 | Feinbert | B68C 1/126 340/573.7 |

\* cited by examiner

*Primary Examiner* — Robert P Bullington

(57) ABSTRACT

A monitoring and feedback device to assist a horse rider in achieving proper balance and posture by measuring one or more load data parameters, such as load magnitude, load angle, or torque, for both stirrups simultaneously and providing visual or audible feedback on that load data to the rider or a non-riding instructor. Load measuring brackets are attached to the stirrup bar of a saddle and each measures one or more of the load data parameters applied. Processing circuitry generates signals for transmitting, either wired or wireless, feedback signals representing the load data to a visual display or sound headset and thereby provides real time information to a rider or non-riding instructor.

17 Claims, 3 Drawing Sheets

EQUESTRIAN MONITORING AND FEEDBACK DEVICE

CROSS REFERENCE TO RELATED APPLICATIONS

This application claims the benefit of U.S. Provisional Patent Application No. 62/067,789 filed Oct. 23, 2014.

BACKGROUND OF THE INVENTION

There are many elements of balance and posture that are relevant to the performance of a horse rider, including points of contact, leg and body position, weight distribution, and movement. Ideally a rider (and that rider's non-riding instructor, if applicable) would be completely aware of all of these elements at all times and would identify any that are not correct. In practice, however, it is very difficult for a rider to sense many of these elements, and over time, improper balance, poor posture and other undesirable habits may arise and become increasingly difficult to identify and address. While an instructor might observe a rider's position and posture, more subtle balance and weight distribution problems may be difficult to observe. For these reasons the need for more accurate measurement of balance and posture data has been recognized. Prior art systems, such as that described in US Patent Application Publication 2013/0280683 (Smith et al.) have attempted to collect a great deal of this data for use in a complex performance sensing system. Another approach, in U.S. Pat. No. 5,369,601 (Tannenbaum), involves the attachment of various sensors to the body of a rider. These prior art systems are cumbersome, expensive, and of questionable usefulness for the vast majority of practical equestrian training settings.

The posture, balance and weight distribution of a rider can be considered around three axes. One axis is parallel to the length of the horse (the X axis) where rotation on this axis would result in the rider leaning side to side (comparable to the "roll" of an aircraft). Another axis (the Y axis) is perpendicular to the length of the horse (parallel to the ground) and, comparable to the "pitch" of an aircraft, rotation around this axis would be reflected by the rider leaning forward or backwards. The third axis (the Z axis) would be vertical up the center of the horse (and the spine of the rider) and Z axis rotation would be reflected by a twisting motion of the rider (corresponding to the "yaw" of an aircraft).

SUMMARY OF THE INVENTION

In this invention meaningful data to assess a rider's balance and posture (and potential errors) around all of the axes described above is obtained by measuring the magnitude and/or angular direction (load angle) of force in the stirrup leathers of a saddle by utilizing load measuring brackets attached to the saddle with the stirrups in turn attached to the load measuring brackets. Load data from the load measuring brackets is processed and feedback signals are provided (either wired or wireless) to a display or audible speaker or headset to be seen or heard by a rider or a non-riding instructor. The present invention focuses on the most critical balance and position elements affecting the largest portion of the equestrian population, especially novice to intermediate riders who may develop poor balance and posture habits, by providing a simple, effective, and affordable device for monitoring and providing feedback on those elements. An objective of this invention is the simultaneous measurement, processing, comparison and display of the load magnitude, load angle and/or torque on both stirrup leathers simultaneously in a manner that allows comparison of the loads to each other. This comparison identifies some of the most significant balance and posture errors, including applying excessive weight to one of the stirrups and twisting inappropriately. The present invention also requires minimal modification to a rider's customary saddle and stirrups and does not interfere with safety features (such as the ability of the stirrup leather to detach from the stirrup bar).

DETAILED DESCRIPTION OF THE INVENTION

Figure 1:
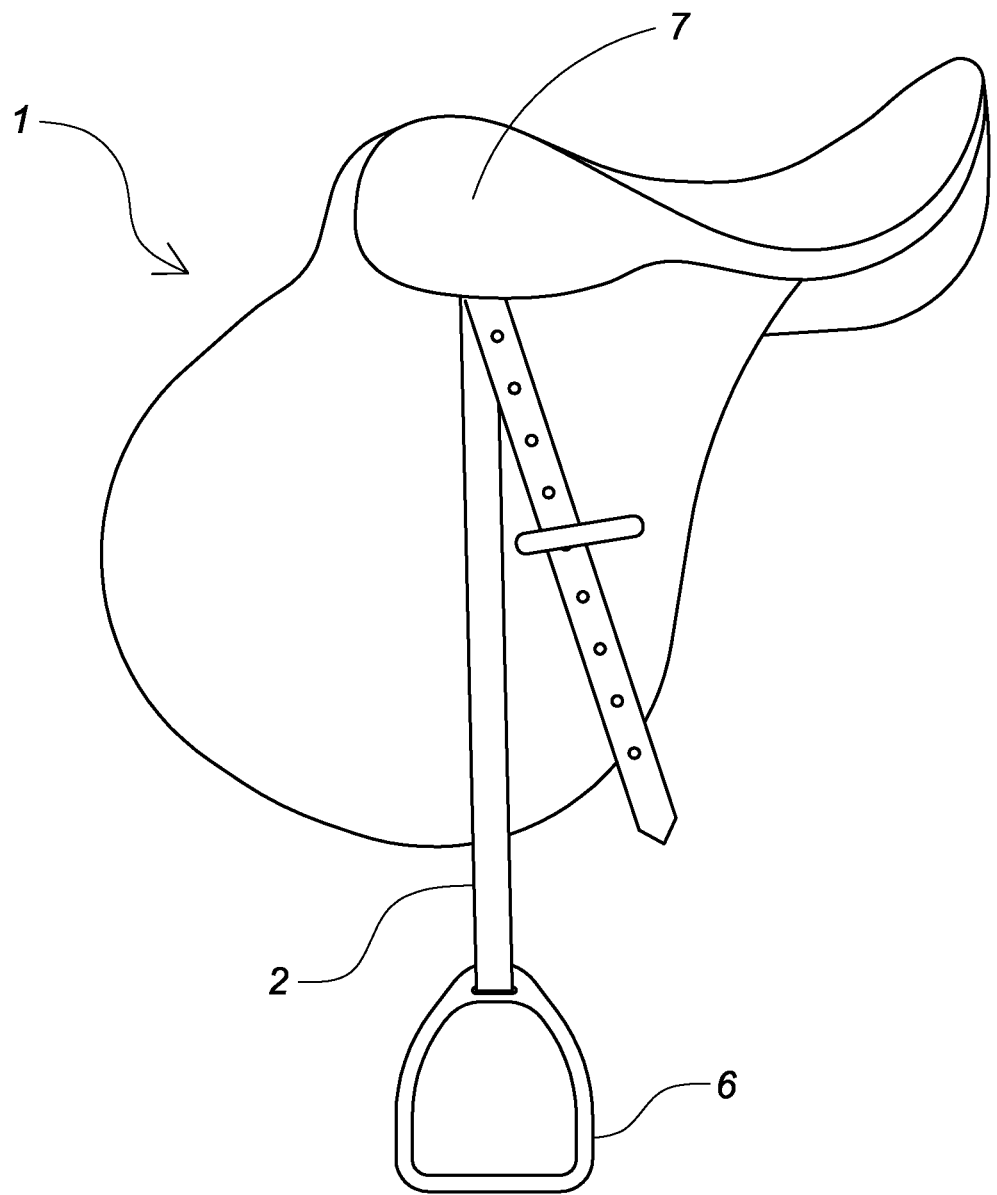
FIG. 1 shows a general view of an English saddle.
Figure 2:
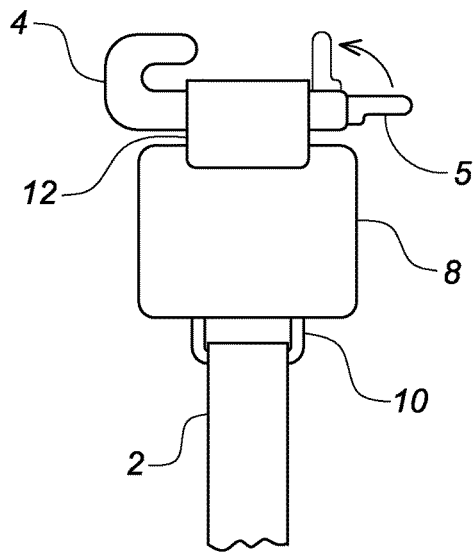
FIG. 2 shows key components of the invention attached to a stirrup bar of a saddle.

As shown in FIG. 1, in an English saddle stirrups attached to a saddle support a portion of the weight of a rider and, particularly in the case of an English saddle, rotate on several axes at the point of attachment. Many aspects of a rider's balance and position can be assessed by analyzing the load magnitude, load angle, and/or torque at this point of attachment of the stirrups to the saddle. Load magnitude, load angle, and/or load torque are referred to collectively as load data. As shown in FIGS. 1 and 2, an English saddle 1 has stirrup leathers 2 attached to a stirrup bar 4 rigidly attached to the saddle. The stirrup bar 4 may include a safety catch 5 that pivots to release the stirrup in an emergency situation to prevent a rider from being dragged by the stirrup. Stirrup irons 6 hang at the end of each stirrup leather 2 and receive the rider's feet. As shown in FIG. 2, in the present invention there are two load measuring brackets 8, each of which is interposed between the saddle stirrup bar 4 and the stirrup leather 2. Each load measuring bracket 8 has an attachment hook 10 to which stirrup leathers 2 are attached. A saddle skirt 7 that is a standard part of an English saddle (see FIG. 1) protects a rider's leg from contact with the stirrup bar 4 and load measuring bracket 8.

A rider's balance relative to the x, y and z axes is reflected in loads of varying magnitudes and angles (relative to an axis) on the stirrups and the corresponding load measuring bracket. In this discussion references to stirrup load refers generally to the force exerted on the stirrup irons by the rider's feet which is correspondingly applied to the stirrup leathers and the load measuring brackets. The key parameters of stirrup load at each load measuring bracket would be force magnitude, force angle (relative to the axes described above) and/or torque. For example, a rider leaning to the left would put greater force load (weight) on the left stirrup than the right, and these forces would be measured by the left and right load measuring brackets. In addition, in the case of a sideways leaning rider, there could be some rotation of the stirrup leathers around the x axis and thus the direction of the force measured at each load measuring bracket would not be purely vertical, but would have both y and z axis components that can be measured at the load measuring brackets.

A rider leaning too far forward, as another example, would cause some rotation of the stirrup leathers back from the point of attachment of the leather to the stirrup bar and this angle of rotation (and/or the x and z axis components of the force load) would be measured by the load measuring brackets. Finally, the stirrup leather may also be subjected to torsional forces if a rider's leg twists around the z (vertical) axis. Torque about the z axis can also be measured at the load measuring bracket. It should be noted that while the leather may not be rigidly attached to the stirrup bar (for safety reasons) and a sufficient rearward force (along the x axis) could detach the leather from the stirrup bar, in typical and even unbalanced riding positions there is sufficient friction between the leather and the stirrup bar to keep the leather stationary and allow rotation of the leather around the stirrup bar attachment point. Generally the attached stirrup leather would be freely rotatable around the x and y axes, at least for some range of rotation, with force load and angle easily measurable in the corresponding directions, but less rotatable around the z axis, and therefore torque measurement would be most appropriate for measuring z axis rotation.

By measuring the load on each stirrup leather and/or the direction of the load relative to the stationary stirrup bar, substantial assessment of a rider's balance and posture is possible. While it is true that not all of the rider's weight would always be fully borne by the stirrup leathers, by simultaneously measuring the relative load on the left and right stirrup leathers and/or the direction of load for each stirrup, a substantially accurate assessment of balance and posture can be made using this invention.

Figure 3:
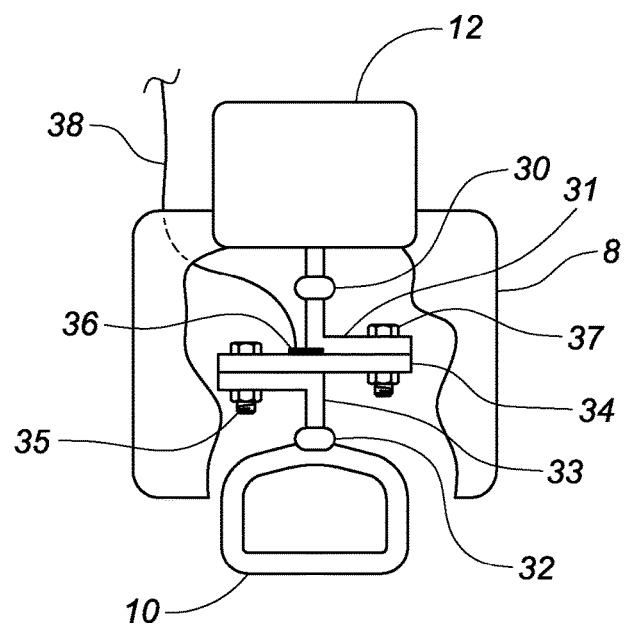
FIG. 3 shows internal components of a preferred load measuring bracket of the invention.

As shown in FIG. 2, the load measuring bracket 8 measures one or more of the load parameters applied to it, such as force magnitude, force angle and/or torque. Devices for electronically measuring these parameters are well known in the art. FIG. 3 shows the internal elements of a load measuring bracket with a simple configuration for measuring load in a single direction. Electronic measurement of the angles between a reference point and a second member are also well known and are described, for example, in U.S. Pat. No. 6,334,257 (Den Ouden) which is incorporated herein by reference. In the case of the present invention, the reference point could be a vertical line corresponding with the z axis and the second member would be the direction of force on the load measuring bracket 8. This angle is sometimes referred to in this description as the load angle. Similarly, electronic torque measurement is well known, such as a torque sensor utilizing strain gauges affixed to a torsion bar as described in U.S. Pat. No. 3,710,874 (Seccombe) which is incorporated herein by reference. Incorporating one or more of these measuring components in the load measuring brackets 8, with one configuration as shown in FIG. 3, enables measurement of force in the stirrup leather, rotation of the leather relative to a desired reference point (vertical, for example) and/or torsional forces around one or more of the desired axes. The relative benefit of additional parameter measurement must be balanced against cost and complexity of the load measuring brackets 8.

In the present invention the preferred parameters for measurement are the force and angle of the load, and most particularly the force in the z (vertical) axis direction (corresponding to the weight of the rider) and/or angle of rotation around the y axis. Since leaning left or right is one of the most common riding position errors, measuring the load magnitude in each stirrup (with or without regard to the specific x, y, or z axis components of the load) by means of the load measuring brackets 8 and comparing the left and right loads is probably the most important measurement comparison. While measurement of multiple parameters of load magnitude, load angle, and/or torque is desirable, measurement of any parameter alone is useful and is intended to be covered by this invention.

It is recognized that stirrup load can vary over time with horse stride and/or rider movement (such as through a posting trot, cantering, stopping, and turning). With data storage components well known in the art, this invention affords the ability to measure, store and display load data over time to permit later review and evaluation over a period of riding, versus just at a single point in time. In addition, the present invention's ability to facilitate analysis of stirrup load graphically over a series of riding movements, speed changes, etc. and to provide real time graphical feedback on the upper and lower limits and timing of stirrup load changes, affords a level of riding analysis previously unattainable.

FIG. 2 shows the primary components of the present invention, viewed from one side of the saddle. There are two load measuring brackets 8, each of which are interposed between the saddle stirrup bar 4 and the stirrup leather 2. Each load measuring bracket 8 has an attachment hook 10 to which stirrup leathers 2 may be attached. The load measuring bracket 8 has means for attachment to the saddle, and more particularly to the stirrup bar 4. In FIG. 2 this means for attachment is shown as a stirrup bar loop 12 that slides over the stirrup bar 4. For safety reasons this stirrup bar loop 12 could slide off the stirrup bar 4 if the rider falls to reduce the risk of the rider being dragged by a stirrup leather 2. The load measuring brackets 8 measure the magnitude and/or angle of the force applied by the stirrup leathers 2. The load measuring brackets 8 should ideally add 1 inch or less to the distance between the stirrup bar 4 and the stirrup leather 2 so that a relatively modest adjustment to the stirrup leather length would be all that would be needed to match the exact configuration of the rider's usual stirrup configuration. It is also desirable that the load measuring brackets 8 rest under the saddle skirt 7 and do not directly contact a rider's leg. Similarly, the thickness of the load measuring bracket 8 should be minimized, ideally less than ¼ inch, so that it is not significantly noticeable to a rider beneath the saddle skirt 7. This unobtrusive structure is particularly important for a competitive rider where consistency in tack is needed for optimal riding performance.

FIG. 3 shows a load measuring bracket with the ability to measure overall force on the bracket (and hence the leather) between two attachment points 30 and 32 on angled members 31 and 33, based on the measurement of deflection of a rigid member 34 using a strain gauge 36 connected by wires 38 to suitable known circuitry. Angled members 31 and 33 are attached to the rigid member 34 with bolts 35 and 37. As discussed above, force magnitude and angle measurement can be achieved using other known electronic measurement technology, in addition to the simple strain gauge-based measurement components shown in FIG. 3. Other measuring approaches utilizing one or more strain gauges, spring scales, torque sensors, and other approaches well known in the art could also be utilized. In addition to the configurations shown in FIG. 3, many other suitable configurations are possible and would be well known to one skilled in the art. The load measuring brackets 8 could be metallic, polymer, or constructed of other materials, but should be designed to withstand substantial and repeated loads since failure could have significant safety implications. The strain gauge approach shown in FIG. 3 is particularly suited to this invention since structural failure of the attachment provided by a suitably designed load measuring bracket is highly unlikely. The load measuring bracket 8 includes a stirrup bar loop 12, which could be a leather, polymer, synthetic or other material comparable to a stirrup leather that would loop over the standard saddle stirrup bar much like a standalone stirrup leather. Any similar structure that would fit over the stirrup bar could be used as the stirrup bar loop. Alternatively, a saddle could be constructed with the present invention permanently incorporated in the saddle, in which case the stirrup bar is also the load measuring bracket.

Figure 4:
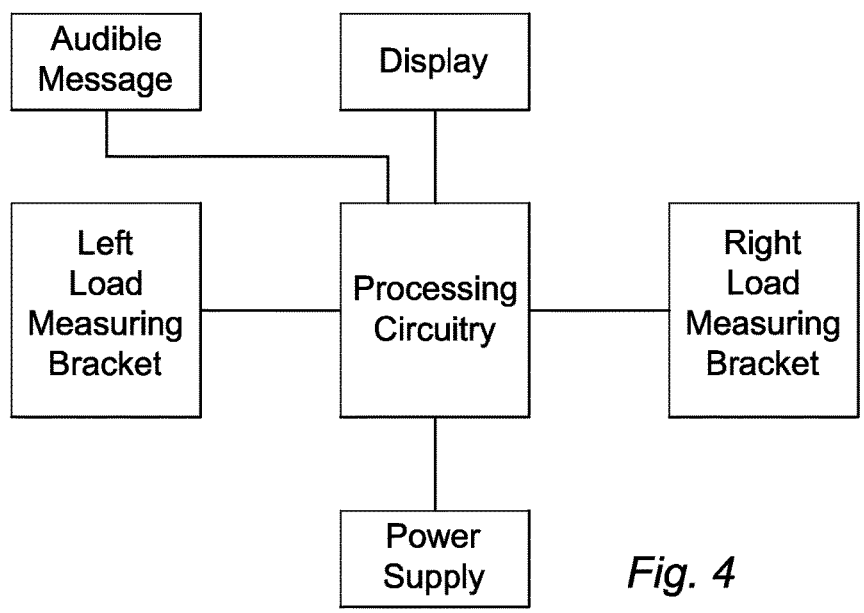
FIG. 4 is a block diagram showing key components of one embodiment of the invention.

As shown in the block diagram in FIG. 4, in a preferred embodiment two load measuring brackets are attached to the right and left sides of saddle, and are electrically connected to circuitry, processors, and electrical components necessary for electrical communication among the load measuring brackets, the power supply and the display or speakers, for the processing of signals representing force data, and for the generation and transmission of feedback signals to generate visual or audio feedback. The specific electrical circuits and components required are well known in the art and are sometimes referred to in this description collectively as processing circuitry, as shown in FIG. 4. At least one power supply is provided, which may be in the proximity of the load measuring brackets or of the processing circuitry. The power supply would include a battery and should be located so as to not interfere with any portion of a rider's legs or body. In a preferred embodiment there is at least one display monitor that would allow a rider and/or a non-riding instructor to see visual feedback on load data. Additionally, as shown in FIG. 4, audio speakers may be utilized to provide audible feedback. The device can be configured to offer audio feedback, visual feedback, or both. There are connections, either wired or wireless, between the load measuring brackets and the processing circuitry and between the processing circuitry and the visual display and/or audio speaker. One configuration would include transmitters (ideally Bluetooth enabled) associated with each load measuring bracket for transmission of load data signals to the processing circuitry which could be attached to the saddle or remote from the saddle (such as associated with a remote display).

Figure 5:
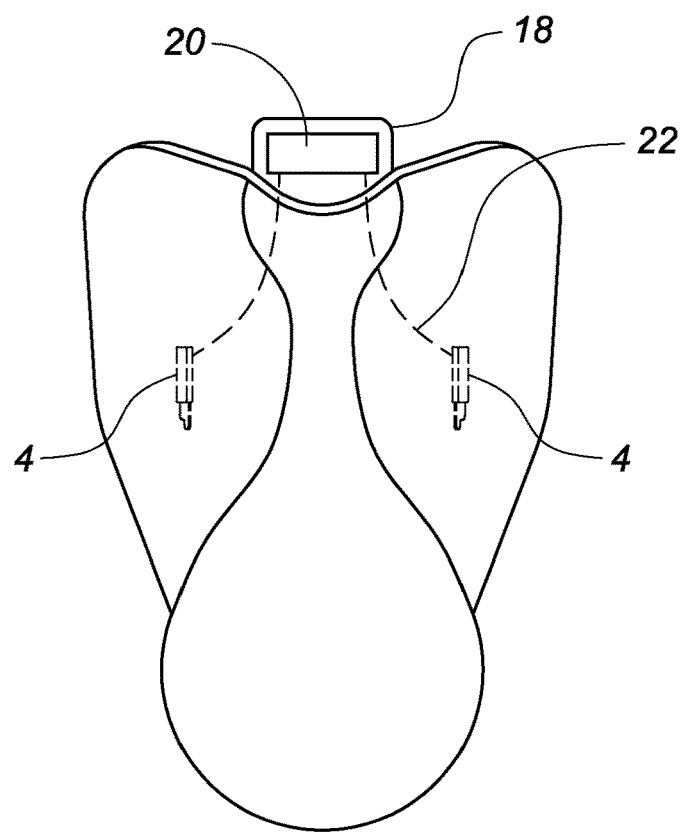
FIG. 5 shows a top view of a saddle and shows the display of the invention.

FIG. 5 shows possible placement of the display monitor 20 and provides a view of the saddle from above. As shown in FIG. 5, the power supply 18 and display monitor 20 could be incorporated into a single base unit that could be attached at the center front of the saddle, resting as needed on the center of the horse's back, with wires 22 used to connect to the load measuring brackets 8. The configuration of an English saddle would make it particularly convenient for these wires to be run from this base unit to each of the load measuring brackets 8, adjacent to the stirrup bars 4, and under the saddle skirts 7 to the front of the saddle in a manner that would not obstruct movement of a rider to a display affixed near the front of a saddle where the display would be readily visible to the rider. These wires could also include a releasing connection that would separate under sufficient load if a rider fell.

Figure 6:
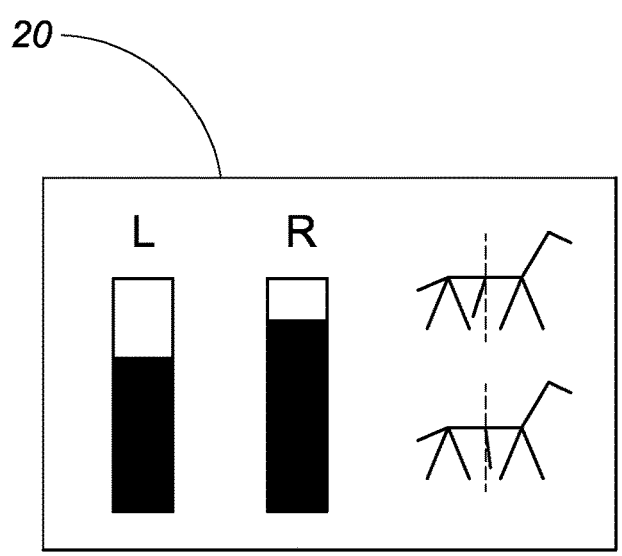
FIG. 6 shows a sample display of the invention.

The display includes appropriate input, processing, programming, display screen, and other customary components to process the signals from the load measuring brackets and display them in an understandable manner to the rider and/or a non-riding instructor. A sample display is shown in FIG. 6. Separate left and right displays are desirable, although other visual representations could also show the degree of improper lean or twist of the rider. The display in FIG. 6 shows left and right relative load and stirrup leather angle of rotation around the y axis. This angle of rotation or load angle can be measured relative to vertical to the horizon (using an inclinometer known in the art) or vertical relative to the y axis center line of the saddle (reflected by the location of the stirrup bars). Calibration of the load measuring brackets is important since accurate comparison of the left and right loads is necessary for proper results.

As noted above, an alternative or additional approach to rider feedback is to provide an audible feedback message to an earphone or headset worn by the rider (or a non-riding instructor). The audible message could be provided via a wired headset or earbud, or could be transmitted to a headset (such as a Bluetooth enabled headset) following the approach described in U.S. Pat. No. 7,062,225 (White), which is incorporated herein by reference. The audible message output circuitry in the invention would be consistent with that described in this referenced patent. The audible message could be, for example, "left load 45 pounds, right load 35 pounds" or "30% more weight on right than left," or a similar message. Furthermore, it would be desirable to provide both audible and visual feedback using a combination of the approaches described above.

The invention could also include one or more transmitters, ideally located adjacent to the power supply or supplies, to transmit data to a remote display or speaker unit that could be used by a non-riding instructor to monitor load data. The remote unit could be a smartphone with a suitable application installed. While there is no requirement that the power supply and the display be part of a single unit, this would be a preferred configuration. It would also be possible to have power supplies (batteries) incorporated into each load measuring bracket. A wireless transmitter could also be incorporated into each load measuring bracket for transmission to a display either adjacent to the saddle for viewing by a rider or to the remote display used by a non-riding instructor. Circuitry and other components for communicating with a remote display are known in the art, such as that described in US Publication No. 2007/0242061 (Rhoten), which is incorporated herein by reference.

In a further enhancement of this invention, two-way communication between a non-riding instructor's remote unit and the base unit would be provided so that an instructor could define a desired level of load (and load angle) for each stirrup leather that would be visually presented on the display of the base unit. It would also be possible in this configuration for an instructor to define a desired reduction (or increase) in the portion of the rider's weight borne by the stirrup leathers versus the legs of the rider at other points of contact with the saddle or horse.

A desirable data communication alternative configuration (one-way or two-way) would utilize a radiofrequency communication link between the load measuring brackets (with its associated circuitry and processing components) or a combined unit for processing signals from both load measuring brackets, and the display unit(s). A radiofrequency link following the Bluetooth protocol, described in detail in US Patent Application Publication US 2004/0203379 (Witkowski) which is incorporated herein by reference, would be particularly suitable for this embodiment of the invention. Utilizing a Bluetooth link and suitable mobile smartphone application programmed by any knowledgeable programmer a user's smartphone could serve as the display of the present invention. The smartphone or other remote display device could further be configured as an input device with which a non-riding instructor could provide defined target load parameters that could be graphically displayed, along with actual load data, on the display viewable by the rider. A Bluetooth enabled connection would be particularly suited for this data input configuration transmitting target load data from the remote device to a receiver associated with the processing circuitry of the present invention.

While this invention has been described with an English saddle, it is also usable with a Western or other saddle type with minor modifications that would be known by one skilled in the art.

I claim:

1. An equestrian monitoring device comprising a load measuring bracket having a means for attachment to a saddle and having an attachment hook for receiving a stirrup leather and said load measuring bracket measuring at least one parameter of load data, and further comprising a power supply and processing circuitry to process load data signals from the load measuring bracket and generate at least one feedback signal.

2. The device in claim 1 further comprising a radiofrequency transmitter for transmitting said at least one feedback signal.

3. The device in claim 1 wherein the load data measured is at least one of load magnitude, load angle, or torque.

4. The device in claim 1 further comprising a display for displaying a visual display corresponding to said at least one feedback signal.

5. The device in claim 1 wherein said at least one feedback signal can generate an audible message providing information on said load data from said load measuring bracket.

6. An equestrian monitoring device comprising two load measuring brackets, each having a means for attachment to a saddle and an attachment hook for receiving a stirrup leather and each of said two load measuring brackets measuring at least one parameter of load data, and further comprising a power supply and processing circuitry to process load data signals from the load measuring brackets and generate at least one feedback signal.

7. The device in claim 6 wherein said at least one feedback signal can generate a visual display presenting said load data from both of said load measuring brackets simultaneously.

8. The device in claim 6 further comprising a radiofrequency transmitter for transmitting said at least one feedback signal.

9. The device in claim 6 wherein the load data measured is at least one of load magnitude, load angle, or torque.

10. The device in claim 6 wherein said at least one feedback signal can generate an audible message providing information on said load data from both of said load measuring brackets.

11. The device in claim 6 wherein said at least one feedback signal is transmitted for receipt and processing by a smartphone having an application capable of generating a display presenting said load data from both of said load measuring brackets simultaneously.

12. The device in claim 6 further comprising data storage components for storing said load data.

13. The device in claim 7 further comprising a receiver for receiving a wireless signal containing target load parameters and said processing circuitry being enabled to process such received signals and display said target load parameters on said visual display.

14. An equestrian monitoring device comprising a load measuring bracket having a means for attachment to a saddle and having an attachment hook for receiving a stirrup leather and said load measuring bracket measuring at least one parameter of load data, and further comprising a power supply and a transmitter for transmitting a signal representing said at least one parameter of load data.

15. The device in claim 14 wherein said at least one parameter of load data is at least one of load magnitude, load angle, or torque.

16. The device in claim 14 further comprising a second load measuring bracket also having a means for attachment to said saddle and measuring said at least one parameter of load data, a second power supply and a second transmitter for transmitting said signal representing said at least one parameter of load data from said second load measuring bracket.

17. The device in claim 16 further comprising a receiver for receiving said signal representing said at least one parameter of load data and a display presenting said at least one parameter of load data from both load measuring brackets simultaneously.

* * * * *